US00PP37382P3

(12) United States Plant Patent
Bull

(10) Patent No.: US PP37,382 P3
(45) Date of Patent: Apr. 21, 2026

(54) ***ECHINACEA* PLANT NAMED 'BullEchipur 122'**

(50) Latin Name: *Echinacea purpurea*
Varietal Denomination: BullEchipur 122

(71) Applicant: Hartwig Bull, Gönnebek (DE)

(72) Inventor: Hartwig Bull, Gönnebek (DE)

(73) Assignee: Hartwig Bull, Gönnebek (DE)

( * ) Notice: Subject to any disclaimer, the term of this patent is extended or adjusted under 35 U.S.C. 154(b) by 0 days.

(21) Appl. No.: 19/235,231

(22) Filed: Jun. 11, 2025

(65) Prior Publication Data

US 2025/0386753 P1 Dec. 18, 2025

Related U.S. Application Data

(60) Provisional application No. 63/731,837, filed on Jun. 12, 2024.

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

(56) References Cited

U.S. PATENT DOCUMENTS

| | | | |
|---|---|---|---|
| 7,982,110 | B2 | 7/2011 | Ren |
| PP31,064 | P2 | 11/2019 | Ren et al. |
| PP35,164 | P2 | 5/2023 | Ren |
| PP35,286 | P3 | 7/2023 | Bull |

OTHER PUBLICATIONS

Brookgreen Gardens *Echinacea purpurea* 'PAS702918', retrieved on Aug. 27, 2025 at https://www.brookgreen.ord/plant-collection/name/echinacea-purpurea-pas702918-powwow%25C2%25AE-white, 3 pages.

ThinkPlants Catalog, 2024-2025, retrieved on Sep. 4, 2025 at https://online.flippingbook.com/view/530070179/34/, 6 pages.

Wist et al., "Floral Structure and Dynamics of Nectar Production in *Echinacea pallida* var. *angustifolia* (*asteraceae*)", Int. J. Plant Sci., 2008, pp. 708-722, vol. 169(6).

*Primary Examiner* — Kent L Bell
(74) *Attorney, Agent, or Firm* — The Webb Law Firm

(57) ABSTRACT

A new and distinct variety of *Echinacea* plant named 'BullEchipur 122' having dark red colored flowers, compact growth habit, uniform growth habit, and 25 to 35 branches.

1 Drawing Sheet

Botanical classification: *Echinacea purpurea.*
Varietal denomination: 'BULLECHIPUR 122'.

BACKGROUND OF THE INVENTION

The present invention relates to a new and distinct cultivar of *Echinacea*, botanically known as *Echinacea purpurea*, and hereinafter referred to by the name 'BullEchipur 122'.

The new *Echinacea* was discovered by the Inventor in August 2021, in a controlled environment in Gönnebek, Germany, as a part of a planned breeding program. The new variety is the result of a controlled cross between an unpatented *Echinacea purpurea* variety having an internal breeder's reference of "Bul 2019-26" (female parent) and an unpatented *Echinacea purpurea* variety having an internal breeder's reference of "Bul 2019-47" (male parent) from the breeder's own collection. The new *Echinacea* was selected on the basis of its dark red colored flowers, compact growth habit, uniform growth habit, and 25 to 35 branches when compared to prior *Echinacea* plants.

Asexual propagation of the new cultivar by in vitro culture cuttings since September 2021, in Gönnebek, Germany, has shown that the unique features of this new *Echinacea* are stable and reproduced true to type in successive generations.

SUMMARY OF THE INVENTION

The following traits have been repeatedly observed and are determined to be unique characteristics of 'BullEchipur 122'. These characteristics in combination distinguish 'BullEchipur 122' as a new and distinct cultivar:

1. Compact growth
2. Dark red flowers
3. 20-30 flowers
4. 25-35 branches
5. Very uniform growth
6. Dark green leaves
7. Fast crop time In side-by-side comparisons conducted by the Inventor in Gönnebek, Germany, plants of the new *Echinacea* differed from plants of the female parent, 'Bul-2019-26' of *Echinacea purpurea*, in the following characteristics:

1. More compact
2. Dark red flower color
3. 25-35 branches
4. Smaller dark green leaves In side-by-side comparisons conducted by the Inventor in Gönnebek, Germany, plants of the new *Echinacea* differed from plants of the male parent, 'Bul-2019-47' of *Echinacea purpurea*, in the following characteristics:

1. Taller growth habit
2. Dark red flower color
3. 25-35 branches
4. 20-30 flowers Plants of the new *Echinacea* can be compared to the plants of the *Echinacea* cultivar 'Tomato Soup', patented as U.S. Plant Pat. No. 19,427 P2. In side-by-side comparisons conducted by the Inventor in Gönnebek, Germany, plants of the new *Echinacea* differed from plants of the cultivar 'Tomato Soup' in the following characteristics:

1. More compact
2. 25-35 branches
3. Very even habit
4. 20-30 flowers
5. Darker red flowers

DESCRIPTION OF THE DRAWINGS

The accompanying colored photograph illustrates the overall appearance of the new *Echinacea*, showing the colors as true as it is reasonably possible to obtain in colored reproductions of this type. Colors in the photograph may differ slightly from the color values cited in the detailed botanical description, which accurately describes the colors of the new *Echinacea*.

FIG. 1 comprises a top perspective view of a typical plant of 'BullEchipur 122' shown under natural lighting.

DESCRIPTION OF THE PLANT

The cultivar *Echinacea* has not been observed under all possible environmental conditions. The phenotype may vary somewhat with variations in environment such as temperature and light intensity without, however, any variance in genotype.

The aforementioned photographs and following observations and measurements describe plants of the new *Echinacea* that were grown in an outdoor nursery in Gönnebek, Germany. During the production of the plants, temperatures averaged about 18-20° C. Plants used for the photographs and description were about 23 weeks from planting. Color references are made to The Royal Horticultural Society Colour Chart, 2015 version, except where general terms of ordinary dictionary significance are used.

PLANT

Botanical classification: *Echinacea purpurea.*

Parentage: "Bul 2019-26" and "Bul 2019-47".

Propagation:

*Time to initiate roots.*—About 7 days.

*Time to develop roots.*—About 40-50 days.

*Time to produce a finished flowering plant.*—About 12-14 weeks.

*Root description.*—Lots of roots, free-branching.

Plant description:

*Growth habit.*—Compact.

*Plant height.*—45-60 cm.

*Plant width.*—35-40 cm.

*Branching habit.*—Lots of branches, upright.

*Lateral branches.*—Number per plant: 25-35. Length: 4-40 cm. Diameter: 3-8 mm. Angle: Upright, outward. Texture: Pubescent. Color: 183A. Internode length: 1-7 cm.

*Foliage.*—Length: 4-21 cm. Width: 1-4.5 cm. Shape: Lanceolate. Shape of Apex: Acuminate. Shape of Base: Attenuate to Acute. Orientation and aspect: Straight to curved. Texture: Upper surface: Rough. Lower surface: Rough. Young leaves: Upper surface color: NN137A. Lower surface color: 137B. Fully expanded leaves: Upper surface color: NN137A. Lower surface color: 137B. Venation: Type: Cross venulate to longitudinal. Color: Upper surface: 145A. Lower surface: 145B. Margin: Entire.

Flowers:

*Bud.*—Stage of opening: Single type blossom.

*Shape.*—Elliptic shaped ray florets and tubular disk floret.

*Diameter.*—1-3.2 cm.

*Length.*—1.2-2.3 cm.

*Color.*—NN137A.

Natural flowering season: 13-14 weeks after planting.

Inflorescence:

*Form.*—Single flower.

*Disc and ray floret arrangement.*—Single composite flower.

*Average number per plant.*—20-30.

*Average number per branch.*—1-3.

*Fragrance.*—None.

*Diameter.*—4-9 cm.

*Height.*—2-3.5 cm.

*Diameter of disc.*—1.5-3.5 cm.

*Receptacle height.*—1 cm.

*Receptacle diameter.*—1.5-3.5 cm.

*Ray florets.*—Number per inflorescence: 16-23. Arrangement: In two or three whorls. Length: 1.5-3.7 cm. Width: 0.9-1.3 cm. Shape: Ellipse. Shape of Apex: Obtuse. Shape of Base: Acute. Margin: Entire. Texture: Upper surface: Smooth, glabrous. Lower surface: Rough. Color: When opening: Upper surface: N45A. Lower surface: 53A. At maturity: Upper surface: N45A. Lower surface: 53A. Ground color description: Red.

*Disc florets.*—Number per inflorescence: Numerous, too many too count. Arrangement: In center of receptacle Length: 8-15 mm. Width: 1-2 mm. Shape: Tubular. Shape of Apex: Acute. Color: Immature: 187A. At maturity: 187A.

*Phyllaries.*—Number per inflorescence: 35-50. Arrangement: In 3 to 4 whorls. Length: 0.5-1.5 cm. Width: 2-3 mm. Shape: Lanceolate. Shape of Apex: Elongate, oval. Shape of Base: Fused. Margin: Entire. Texture: Upper surface: Rough. Lower surface: Rough. Color: Immature: Upper surface: NN137B. Lower surface: NN137B. At maturity: Upper surface: NN137B. Lower surface: NN137B.

Reproductive organs:

*Androecium.*—Presence: On disk florets. Number: One. Filament: Length: 1-2 mm. Color: 187B. Anther: Shape: Oval. Length: 1 mm. Color: 187B. Pollen: Color: 15B.

*Gynoecium.*—Presence: In disk and ray florets. Pistil length: 1-2 mm. Stigma: Shape: Two parted. Color: 187A. Style: Length: 1-2 mm. Color: 187A.

*Seeds/fruit.*—Length: 1-2 mm.

Disease/pest resistance:

*Disease resistance.*—No disease resistance has been observed.

*Pest resistance.*—No pest resistance has been observed.

Weather tolerance:

*Temperature tolerance*.—No temperature resistance has been observed.

*Drought tolerance*.—No drought resistance has been observed.

I claim:

1. A new and distinct cultivar of *Echinacea* plant named 'BullEchipur 122', as herein illustrated and described.

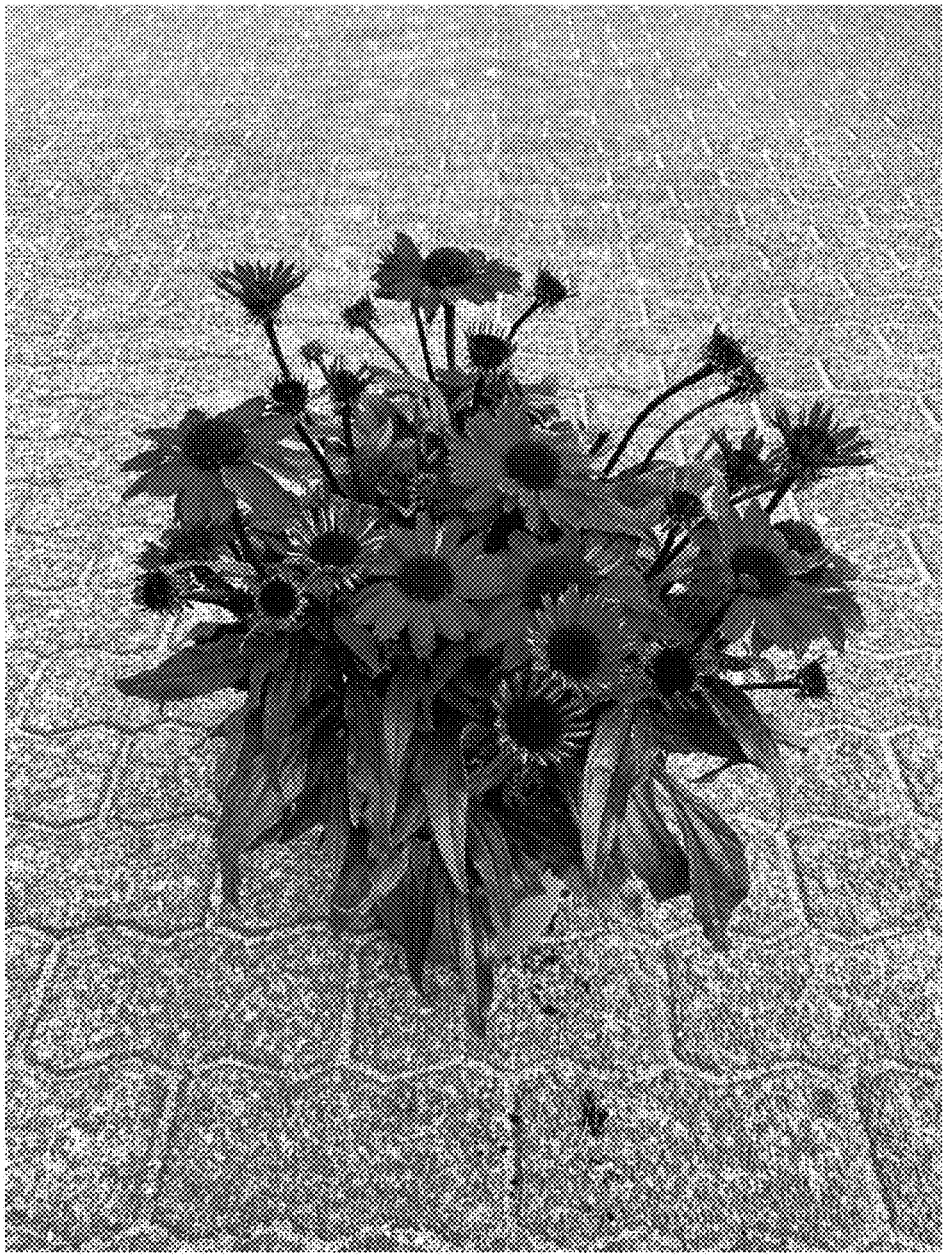

* * * * *